United States Patent [19]

Laurent et al.

[11] 4,049,804

[45] Sept. 20, 1977

[54] NOVEL PREGNANOIC ACID DERIVATIVES

[75] Inventors: Henry Laurent; Klaus Annen; Rudolf Wiechert; Helmut Hofmeister, all of Berlin, Germany

[73] Assignee: Schering Aktiengesellschaft, Berlin & Bergkamen, Germany

[21] Appl. No.: 668,394

[22] Filed: Mar. 19, 1976

[30] Foreign Application Priority Data

| Mar. 21, 1975 | Germany | 2513558 |
|---|---|---|
| Mar. 21, 1975 | Germany | 2513555 |
| Mar. 21, 1975 | Germany | 2513557 |
| Mar. 21, 1975 | Germany | 2513556 |

[51] Int. Cl.$^2$ .................. A61K 31/56; C07J 21/00
[52] U.S. Cl. .................. 424/242; 260/397.1; 260/239.55 D
[58] Field of Search .................. 260/397.1

[56] References Cited

U.S. PATENT DOCUMENTS

| 3,833,563 | 9/1974 | Laurent et al. | 260/397.1 |
| 3,856,828 | 12/1974 | Phillipps et al. | 260/397.1 |
| 3,906,095 | 9/1975 | Laurent et al. | 260/397.1 |
| 3,944,577 | 3/1976 | Laurent et al. | 260/397.1 |

*Primary Examiner*—Elbert L. Roberts
*Attorney, Agent, or Firm*—Millen & White

[57] ABSTRACT

Pregnanoic acid derivatives of general formula

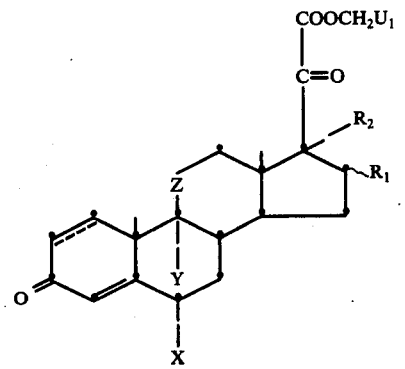

wherein ---- is a single bond or a double bond; X is hydrogen, fluorine or methyl; Y is hydrogen, fluorine or chlorine; Z is $\beta$-hydroxymethylene, $\beta$-acyloxymethylene, $\beta$-fluoromethylene, $\beta$-chloromethylene, carbonyl or methylene; $R_1$ is hydrogen, methyl in the $\alpha$- or $\beta$-position or methylene and $R_2$ is hydrogen, hydroxy or acyloxy, or $R_1$ and $R_2$ collectively are alkylidendioxy and $U_1$ is halogen, halogenated alkyl of 1–5 carbon atoms or halogenated phenyl, are topically effective anti-inflammatory agents.

81 Claims, No Drawings

NOVEL PREGNANOIC ACID DERIVATIVES

BACKGROUND OF THE INVENTION

This invention relates to novel pregnanoic acid compounds having outstanding anti-inflammatory activity following topical application to inflamed areas of a mammalian body.

SUMMARY OF THE INVENTION

In a composition aspect, this invention relates to novel pregnanoic acid compounds of Formula I

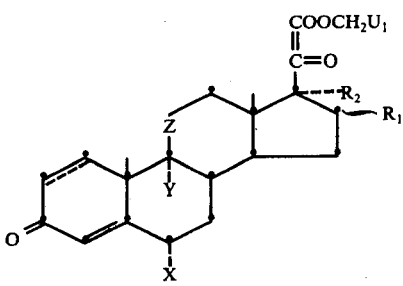

wherein ---- is a single bond or a double bond; X is hydrogen, fluorine or methyl; Y is hydrogen, fluorine or chlorine; Z is β-hydroxymethylene, β-alkanoyloxymethylene of 1-8 carbon atoms in the alkanoyl, β-fluoromethylene, β-chloromethylene, carbonyl or methylene; $R_1$ is hydrogen, methyl in the α- or β-position or methylene and $R_2$ is hydrogen, hydroxy, alkanoyloxy of 1-8 carbon atoms or benzoyloxy or $R_1$ and $R_2$ collectively are alkylidendioxy of up to 6 carbon atoms; and $U_1$ is halogen, halogenated alkyl of 1-5 carbon atoms, or halogenated phenyl.

In another compositional aspect, this invention relates to a topically-effective anti-inflammatory pharmaceutical preparation, comprising a compound of Formula I, in admixture with a pharmaceutically acceptable carrier.

In a method-of-use aspect, this invention relates to a method of treating mammals afflicted with skin diseases comprising applying to the diseased area an amount of a compound of Formula I, in admixture with a pharmaceutically acceptable carrier, effective to alleviate inflammation caused by the skin disease.

In a preparative aspect, this invention relates to preparing a pregnanoic acid compound of Formula I, wherein $U_1$ is halogenated phenyl, comprising treating a compound of the Formula A

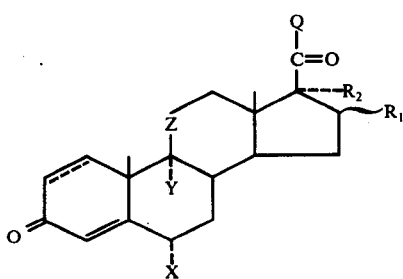

wherein Q is formyl, including hydrates and hemiacetals thereof, with an aliphatic alcohol of the formula HO—$CH_2U_2$ wherein $U_2$ is halogenated alkyl of 1-5 carbon atoms or halogenated phenyl.

In a further compositional aspect, this invention relates to novel 20-hydroxy-pregnanoic acid compounds of the Formula IV

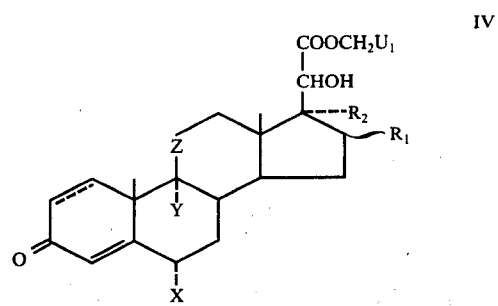

wherein ---- X, Y, Z, $R_1$, $R_2$ and $U_1$ are as above.

DETAILED DISCUSSION

An alkylidenedioxy group $R_1$ and $R_2$ is to mean preferably an alkylidenedioxy group of 3-6 carbon atoms. Examples of possible alkylidenedioxy groups are the isopropylidenedioxy group, the 2,2-butylidenedioxy group or the 3,3-pentylidenedioxy group.

A β-acyloxymethylene group Z and an acyloxy group $R_2$ is understood to mean preferably a group derived from a carboxylic acid of 1-8 carbon atoms, such as formic acid, acetic acid, propionic acid, butyric acid, valeric acid or caproic acid.

A halogen atom $U_1$ is to mean a fluorine atom, a chlorine atom, a bromine atom, or an iodine atom. A halogenated alkyl group of 1-5 carbon atoms is understood to represent preferably a group of the empirical formula $C_nH_{2n+1-m}U_m$ wherein U stands for fluorine, chlorine, bromine or iodine and n means the numbers from 1 to 5, and m means the numbers from 1 to 3. Preferred groups are those wherein the halogen atoms are bound to a carbon atom. Preferably, a halogenated alkyl group $U_1$ is to mean a halogenated methyl group.

Examples for halogenated alkyl groups are: The fluoromethyl group, the trifluoromethyl group, the chloromethyl group, the dichloromethyl group, the trichloromethyl group, the bromomethyl group and the iodomethyl group.

A halogenated phenyl group is understood to mean preferably a phenyl group carrying 1-3 halogen atoms. Examples for halogenated phenyl groups are: The o-, m- and p-fluorophenyl group, the o-, m- and p-chlorophenyl group, as well as the 2,4-, 3,4- and 2,6-dichlorophenyl group.

Of compounds of Formula I, those which are particularly preferred are compounds wherein, in formula I:
 a. $U_1$ is halogen;
 b. $U_1$ is fluorine or chlorine;
 c. $U_1$ is halogenated alkyl of 1-5 carbon atoms;
 d. $U_1$ is fluoromethyl, chloromethyl, trifluoromethyl or trichloromethyl;
 e. $U_1$ is halogenated phenyl;
 f. $U_1$ is p-fluorophenyl;
 g. Z is β-hydroxymethylene, including (a) – (f);
 h. Z is β-alkanoyloxymethylene of 1-8 carbon atoms in the alkanoyl, including (a) – (f);
 i. Z is carbonyl, including (a) – (f);
 j. Z is β-fluoromethylene or β-chloromethylene, including (a) – (f);

k. Z is methylene, including (a) – (f);

l. $R_1$ is hydrogen, methyl in the α- or β-position or methylene and $R_2$ is hydrogen, hydroxy or alkanoyloxy of 1–8 carbons, including (a) – (k);

m. $R_1$ and $R_2$ collectively are alkylidendioxy of up to 6 carbon atoms, including (a) – (k);

n. $R_1$ and $R_2$ collectively are alkylidenedioxy of 3–6 carbon atoms, including (a) – (k); and o. $R_1$ and $R_2$ collectively are isopropylidenedioxy, including (a) – (k).

The compounds of this invention can be prepared in accordance with a process which is characterized in that, in a conventional manner, a. a pregnanoic acid derivative of general Formula II

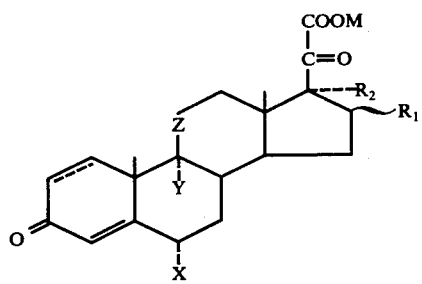

II wherein ===== X, Y, Z, $R_1$ and $R_2$ have the above-indicated meanings and M represents an alkali metal atom or a silver(I) atom, is reacted with a halogenide of general Formula III

WCH$_2$U$_1$                                     III wherein $U_1$ has the above-indicated meanings and W is a halogen atom having a higher atomic weight than the halogen atoms in $U_1$; or b. the 20-hydroxy group of a pregnanoic acid derivative of general Formula IV is oxidized

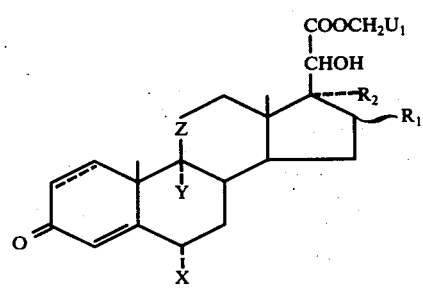

IV wherein ===== X, Y, Z, $R_1$, $R_2$ and $U_1$ have the above-indicated meanings;

c. a pregnane derivative of general Formula V

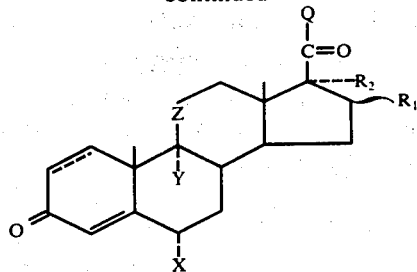

V wherein ===== X, Y, Z, $R_1$ and $R_2$ have the above-indicated meanings and Q represents a formyl group, a carboxyl group, a chlorocarbonyl group, or an alkoxycarbonyl group, is reacted optionally in the presence of an oxidation agent, with an alcohol of general Formula VI

HO—CH$_2$U$_2$                                    VI wherein $U_2$ represents a halogenated alkyl group of 1–5 carbon atoms or a halogenated phenyl group; or d. in a pregnanoic acid derivative of general Formula VII

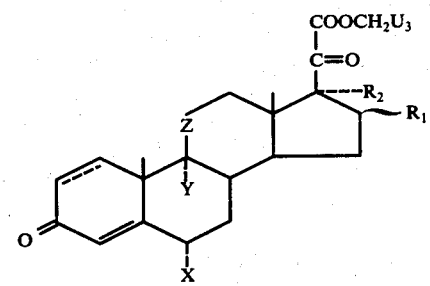

VII wherein ===== X, Y, Z, $R_1$ and $R_2$ have the above-indicated meanings, and $U_3$ represents a hydroxyalkyl group of 1–5 carbon atoms, the hydroxy group present in $U_3$ is exchanged with a halogen atom; and optionally the halogen atoms present in $U_1$ are exchanged with other halogen atoms.

The process of this invention according to method (a) is conducted under the conditions usually employed for the reaction of alkali metal or silver salts of carboxylic acids with halogenated hydrocarbons. Thus, it is possible, for example, to react the alkali metal salts of general Formula II (preferably the lithium salts, the sodium salts, or the potassium salts) in a polar solvent, such as a ketone (acetone, methyl ethyl ketone, methyl isobutyl ketone, etc.) or in a dipolar aprotic solvent (such as dimethylformamide, N-methylacetamide, N-methylpyrrolidone, acetonitrile, hexamethylphosphoric triamide, etc.) at a reaction temperature of between about 20° C. and 150° C. with the halogenide of general Formula III. It is advantageous in this reaction to utilize an excess of the halogenide of general Formula III; thus, per mole of compound II, about 2–50 moles of halogenide of general Formula III is advantageously employed.

The pregnanoic acid derivatives of general Formula I can be prepared from the corresponding 20-hydroxy compounds of general Formula IV by oxidizing the latter compounds in an inert solvent with manganese(IV) oxide or lead(IV) oxide according to the process described in DOS German Unexamined Laid-Open application No. 2,204,361.

The process of this invention according to alternative (b) can be conducted in those inert solvents which are customarily employed in the steroid chemistry for oxidation reactions. Suitable solvents are, for example: hydrocarbons, such as cyclohexane, benzene, toluene, or xylene; chlorinated hydrocarbons, such as methylene chloride, chloroform, carbon tetrachloride, tetrachloroethylene, or chlorobenzene; ketones, such as acetone, methyl ethyl ketone, methyl isobutyl ketone, or acetophenone; or preferably ethers, such as diethyl ether, diisopropyl ether, dibutyl ether, tetrahydrofuran, dioxane, or glycol dimethyl ether and/or alcohols, such as methanol, ethanol, isopropanol, or tert.butanol. The process of this invention can also be conducted in mixtures of the aforementioned solvents.

The process of this invention in accordance with method (b) can be conducted with the use of manganese(IV) oxide or lead(IV) oxide. For this mode of operation, active manganese(IV) oxide is preferably employed, as usual in steroid chemistry during oxidation reactions.

The reaction according to this alternative (b) is preferably accomplished at a reaction temperature of between 0° C. and 50° C. To determine the optimum reaction time, it is advantageous to withdraw, in a preliminary experiment, samples from the reaction mixture at chronological intervals and examine these samples analytically, e.g. by means of thin-layer chromatography. The optimum reaction time is dependent on the structure of the 20-hydroxy compounds employed and is normally 5-30 minutes, if the reaction is conducted at room temperature.

It is possible to prepare the pregnanoic acid derivatives of general Formula I from compounds of general Formula V with Q meaning a formyl group, in accordance with variant (c), by reacting such compounds in a lower alcohol with an amount, required for the reaction, of an oxidizing heavy metal salt, such as, for example, silver oxide, lead(IV) oxide, minium, vanadium(V) oxide, or active manganese(IV) oxide; however, the amounts of desired product obtained during this reaction are normally unsatisfactory. Surprisingly, relatively good yields of the products of this process are attained by oxidizing the compounds of general Formula V with Q signifying a formyl group, or the hydrates or hemiacetals thereof, according to process alternative (c), in a lower aliphatic alcohol containing cyanide ions and being buffered to pH 4-7, with the aid of atmospheric oxygen or manganese(IV) oxide.

For this process variant according to the invention, active manganese(IV) oxide is employed as used customarily for oxidation reactions (L.F. Fieser and M. Fieser, Reagents for Organic Synthesis; John Wiley and Sons, Inc., New York, London, Sydney 1967, pp. 637 et seq.).

This reaction is conducted with the use of cyanide ions as the catalyst. Reagents yielding cyanide ions are preferably alkali cyanides, such as sodium or potassium cyanide. Preferably, 0.01 mole to 10 moles and especially 0.1 - 1.0 mole of cyanide is utilized per mole of compound V. If alkali cyanides are used as the reagents yielding cyanide ions, the reaction is conducted by furthermore adding to the reaction mixture the amount of mineral acid (e.g. sulfuric acid, phosphoric acid, or hydrogen chloride), sulfonic acid (such as p-toluenesulfonic acid), or carboxylic acid (such as formic acid or acetic acid) required for buffering the alkali cyanide.

This variant of the process is preferably conducted in the presence of dipolar aprotic solvents. Suitable dipolar aprotic solvents are, for example: dimethylformamide, N-methylacetamide, dimethylacetamide, N-methylpyrrolidone, dimethyl sulfoxide, sulfolane, dimethylsulfone, hexamethylphosphoric triamide, or n-alkyl cyanides of 1-5 carbon atoms in the alkyl residue, such as acetonitrile.

The reaction is suitably conducted by using, as the solvent, per gram of compound V 2 ml. - 200 ml. of a mixture consisting of 5-50% of a lower alcohol and 50-95% of a dipolar aprotic solvent.

The reaction is suitably accomplished at a reaction temperature of between −20° C. and +100° C., preferably at a reaction temperature of between 0° C. and +50° C. The reaction time is dependent on the reaction temperature and the choice of reactants and is, on the average, when using atmospheric oxygen 5-120 minutes and when using active manganese(IV) oxide 1-30 minutes.

The esterification of compounds of general Formula V with Q meaning a carboxyl group or a chlorocarbonyl group is likewise effected in accordance with conventional methods.

A generally applicable method is the reaction of the acids with the alcohols in the presence of carbonyl diimidazole, dicyclohexyl carbodiimide, or trifluoroacetic anhydride.

Furthermore, the acids can be reacted with the alcohols or the lower-alkanecarboxylic acid esters of the alcohols in the presence of strongly acidic catalysts, such as hydrogen chloride, sulfuric acid, perchloric acid, trifluoromethylsulfonic acid, or p-toluenesulfonic acid. On the other hand, it is also possible to react the acid chlorides in the presence of alkaline catalysts, such as pyridine, collidone, lutidene, 4-dimethylaminopyridine, with the alcohols.

Furthermore, the 21-alkyl esters corresponding to general Formula I are to be reacted with the finally desired alcohol. This reaction is preferably conducted at a reaction temperature of between 50° C. and 180° C. During this reaction, the finally desired alcohol is used in an excess; preferably, 10 - 1,000 moles of alcohol is used per mole of steroid. The alcohol can optionally be diluted with additional solvents, such as, for example, ethers, e.g. di-n-butyl ether, tetrahydrofuran, dioxane, glyciol dimethyl ether, or dipolar aprotic solvents, such as dimethylformamide, N-methylacetamide, dimethyl sulfoxide, N-methylpyrrolidone, or acetonitrile.

If the starting compounds employed are acids, acid chlorides, or esters differing from those of general Formula V in that they carry a 20-hydroxy group, then it is possible to synthesize, with the aid of the aforedescribed methods, the unknown starting compounds of process variant (b).

The process of this invention according to method (d) is likewise accomplished in a conventional manner.

A preferred method for exchanging the hydroxy group resides an esterifying the hydroxy group with a sulfonic acid, preferably with methanesulfonic acid or p-toluenesulfonic acid, and subsequently exchanging the sulfonic acid group with halogen. The hydroxy group is esterified, for example, by treating the compounds of Formula VII with a sulfonic acid chloride in the presence of an organic base, such as pyridine, or in the presence of aqueous alkalis. The exchange of the sulfonic acid group with a halogen atom takes place preferably by reacting the sulfonic acid esters in a polar solvent at about 50°–180° C. with an alkali halogenide, such as potassium hydrogen fluoride or lithium chloride. Suitable polar solvents are ketones, such as acetone or methyl ethyl ketone, and dipolar aprotic solvents, such as dimethylformamide, dimethylacetamide, hexamethylphosphoric triamide, or N-methylpyrrolidone; optionally, minor amounts of protonic solvents are added, such as methanol, ethanol, or water.

The optionally following exchange of the halogen atoms in group $U_1$ can be conducted under the same conditions as utilized for exchanging the sulfonic acid residues with halogen atoms.

Furthermore, the fluorine compounds of general Formula I can also be prepared from the corresponding bromine or iodine compounds by reaction with silver fluoride.

However, the above-described methods are only suitable for the exchange of those sulfonic acid residues and halogen atoms which are not bound to a phenyl residue.

The novel preganonic acid derivatives of general Formula I are pharmacologically active substances distinguished in particular by a pronounced anti-inflammatory effectiveness upon topical administration, while they are practically inactive systemically. Moreover, these compounds are often distinguished by a rapid onset of effectiveness, a high intensity of activity, and a long duration of effectiveness; they have frequently a favorable resorbability and a relatively good stability in galenic preparations.

The novel compounds are suitable in combination with the carriers customary in galenic pharmacy for the local treatment of contact dermatitis, eczemas of a great variety of types, neurodermatitis atopica, erythrodermia, burns, pruritus vulvae et ani, rosacea, erythematodes cutaneus, psoriasis, lichen ruber planus et verrucosus, and similar skin diseases.

The special medicinal agents are prepared by converting the active agents together with suitable additives into the desired form of application, such as, for example, solutions, lotions, ointments, creams, or plasters. In the thus-formulated medicines, the concentration of active agent is dependent on the form of application. In case of lotions and ointments, an effective agent concentration of 0.001% to 1% is preferably utilized.

Moreover, the novel compounds are also highly suitable for the preparation of inhalants, optionally in combination with the customary carriers and auxiliary agents.

Suitable additives are pharmaceutically acceptable organic or inorganic carrier substances suitable for topical application which do not deleteriously react with the active compounds, including but not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For topical application, these are employed as non-sprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 5.0 g. of $11\beta,17\beta,21$-trihydroxy-1,4-pregnadiene-3,20-dione is dissolved in 500 ml. of methanol and combined with a suspension of 1.25 g. of copper(II) acetate in 500 ml. of methanol. The mixture is stirred for 2 hours at room temperature while introducing air into the mixture, and then is diluted with methylene chloride. The mixture is washed with ammonium chloride solution and water; the organic phase is dried over sodium sulfate and concentrated under vacuum, thus obtaining 5.0 g. of $11\beta,17\beta$-dihydroxy-3,20-dioxo-1,4-pregnadien-21-al as a crude product.

b. 2.5 g. of $11\beta,17\beta$-dihydroxy-3,20-dioxo-1,4-pregnadien-21-al is dissolved in 25 ml. of dimethylformamide and combined with 9 ml. of 2-chloroethanol, 5 g. of active manganese(IV) oxide, 2.5 ml. of concentrated acetic acid, as well as 400 mg. of potassium cyanide; the mixture is agitated for 4 minutes at room temperature. The reaction mixture is vacuum-filtered, the residue is washed out with chloroform, the organic phase is washed with water, dried with sodium sulfate, and concentrated under vacuum. The crude product is chromatographed on silica gel. With 31–39% ethyl acetate-hexane and after recrystallization from acetone/petroleum ether (60°–80° C), 785 mg of the 2-chloroethyl ester of $11\beta,17\beta$-dihydroxy-3,20-dioxo-1,4-pregnadien-21-oic acid is obtained; m.p 198.5° C. $[\alpha]_D^{25} = +97°$ (chloroform). UV: $\epsilon_{243} = 15,000$ (methanol).

EXAMPLE 2

750 mg. of $11\beta,17\alpha$-dihydroxy-3,20-dioxo-1,4-pregnadien-21-al is converted into the 2-fluoroethyl ester of $11\beta,17\alpha$-dihydroxy-3,20-dioxo-1,4-pregnadien-21-oic acid in accordance with the conditions described in Example 1(b) but with the use of 2-fluoroethanol. Yield: 137 mg.; m.p. 207.2° C. $[\alpha]_D^{25} = +76°$ (chloroform). UV: $\epsilon_{242} = 15,100$ (methanol).

EXAMPLE 3

1.0 g. of the $9\alpha$-fluoro-$11\beta,17\alpha$-dihydroxy-$16\alpha$-methyl-3,20-dioxo-1,4-pregnadien-21-al prepared in accordance with Example 1(a) is reacted in correspondence with Example 1(b) to obtain 245 mg. of the 2-chloroethyl ester of $9\alpha$-fluoro-$11\beta,17\alpha$-dihydroxy-$16\alpha$-methyl-3,20-dioxo-1,4-pregnadien-21-oic acid. $[\alpha]_D^{25} = +45°$ (pyridine). UV: $\epsilon_{237} = 14,900$ (methanol).

EXAMPLE 4 a. 2.8 g. of 11β,17α-dihydroxy-3,20-dioxo-1,4-pregnadien-21-al is dissolved in 90 ml. of methylene chloride and 50 ml. of methanol and combined with 3 ml. of concentrated acetic acid and 700 mg. of potassium cyanide. The reaction mixture is stirred for 15 minutes at room temperature, then diluted with methylene chloride and washed with water. The organic phase is dried over sodium sulfate and evaporated. The residue is chromatographed on silica gel, and recrystallization from acetone/hexane yields 433 mg. of the methyl ester of 11β,17α-dihydroxy-3,20-dioxo-1,4-pregnadien-21-oic acid, m.p. 215.5° C. $[\alpha]_D^{25} = +72°$ (pyridine).

b. 400 mg. of the methyl ester of 11β,17α-dihydroxy-3,20-dioxo-1,4-pregnadien-21-oic acid is dissolved in 50 ml. of methanol containing about 10% water. Under the exclusion of oxygen, the solution is combined with 0.5 ml. of 2N sodium hydroxide solution, diluted with water after 30 minutes, and extracted with methylene chloride. The aqueous phase is acidified with hydrochloric acid and then extracted with diethyl ether. The ether extract is dried and evaporated under vacuum. The residue is recrystallized from methylene chloride/diisopropyl ether, thus producing 178 mg. of 11β,17α-dihydroxy-3,20-dioxo-1,4-pregnadien-21-oic acid; m.p. above 300° C.

c. 150 mg. of 11β,17α-dihydroxy-3,20-dioxo-1,4-pregnadien-21-oic acid is dissolved in 25 ml. of methanol and combined with 4.0 ml. of a 0.1N solution of sodium hydroxide in methanol. The solution is extensively concentrated under vacuum and the residue combined with 25 ml. of ether. The thus-precipitated sodium salt of 11β,17α-dihydroxy-3,20-dioxo-1,4-pregnadien-21-oic acid is vacuum-filtered and dried under vacuum; yield: 160 mg.

d. A solution of 160 mg. of the sodium salt of 11β,17α-dihyroxy-3,20-dioxo-1,4-pregnadien-21-oic acid in 2.5 ml. of hexamethylphosphoric triamide is combined with 0.2 ml. of chloroiodomethane and stirred for 20 minutes at room temperature. After dilution with ethyl acetate, the reaction mixture is washed neutral with water and dried over sodium sulfate, whereupon it is concentrated under vacuum. The residue is purified with the aid of preparative layer chromatography, thus obtaining 47 mg. of the chloromethyl ester of 11β,17α-dihydroxy-3,20-dioxo-1,4-pregnadien-21-oic acid.

EXAMPLE 5

A solution of 100 mg. of the chloromethyl ester of 11β,17α-dihydroxy-3,20-dioxo-1,4-pregnadien-21-oic acid in 10 ml. of acetonitrile is combined with 250 mg. of silver fluoride and stirred for 4 days at room temperature. After filtering, the solution is diluted with ethyl acetate, washed repeatedly with water, dried, and concentrated under vacuum. Preparative thin-layer chromatography yields the fluoromethyl ester of 11β,17α-dihydroxy-3,20-1,4-pregnadien-21-oic acid.

EXAMPLE 6

1.0 g. of 9α-fluoro-11β,17α-dihydroxy-16β-methyl-3,20-dioxo-1,4-pregnadien-21-al produced in accordance with Example 1(a) is reacted analogously to Example 1(b) to 270 mg. of the 2-chloroethyl ester of 9β-fluoro-11α,17β-dihydroxy-16β-methyl-3,20-dioxo-1,4-pregnadien-21-oic acid.

EXAMPLE 7

400 mg. of 11β,17α-dihydroxy-3,20-dioxo-6α-methyl-1,4-pregnadien-21-al produced in correspondence with Example 1(a) is converted into 103 mg. of the 2-fluoroethyl ester of 11β,17α-dihydroxy-3,20-dioxo-6α-methyl-1,4-pregnadien-21-oic acid under the conditions described in Example 1(b) with 2-fluoroethanol.

EXAMPLE 8

500 mg. of 11β,17α-dihydroxy-3,20-dioxo-16-methylene-1,4-pregnadien-21-al prepared in accordance with Example 1(a) is converted, in correspondence with the conditions set forth in Example 1(b), into 160 mg. of the 2-chloroethyl ester of 11β,17α-dihydroxy-3,20-dioxo-16-methylene-1,4-pregnadien-21-oic acid.

EXAMPLE 9

1.0 g. of the methyl ester of 11β,17α-dihydroxy-3,20-dioxo-1,4-pregnadien-21-oic acid is dissolved in 20 ml. of 2-chloroethanol and stirred for 5 days at room temperature. The reaction product is thereafter precipitated with water, vacuum-filtered, dried, and chromatographed on silica gel, thus obtaining 317 mg. of the 2-chloroethyl ester of 11β,17α-dihydroxy-3,20-dioxo-1,4-pregnadienn-21-oic acid.

EXAMPLE 10

500 mg. of 11β,17α-dihydroxy-3,20-dioxo-1,4-pregnadien-21-al is converted, under the conditions set forth in Example 1(b) but with 2,2,2-trifluoroethanol, into the 2,2,2-trifluoroethyl ester of 11 β,17α-dihydroxy-3,20-dioxo-1,4-pregnadien-21-oic acid.

EXAMPLE 11

500 mg. of 11β,17αdihydroxy-3,20-dioxo-1,4-pregnadien-21-al is converted, under the conditions described in Example 1(b) but with the use of 2,2,2-trichloroethanol, into the 2,2,2-trichloroethyl ester of 11β,17α-dihydroxy-3,20-dioxo-1,4-pregnadien-21-oic acid.

EXAMPLE 12

500 mg. of 11β,17α-dihydroxy-3,20-dioxo-1,4-pregnadien-21-al is converted, under the conditions disclosed in Example 1(b) but with 4-fluorobenzyl alcohol, into the 4-fluorobenzyl ester of 11β,17α-dihydroxy-3,20-dioxo-1,4-pregnadien-21-oic acid.

EXAMPLE 13 a. 2.0 g. of 11β,21-dihydroxy-17α-butyryloxy-4-pregnene-3,20-dione is dissolved in 150 ml. of methanol and combined with 1.2 g. of copper(II) acetate. The solution is agitated for 2 hours while passing air therethrough. The reaction mixture is diluted with methylene chloride, washed with ammonium chloride solution and water, dried over sodium sulfate, and concentrated under vacuum, thus obtaining 2.17 g. of 11β-hydroxy-17α-butyryloxy-3,20-dioxo-4-pregnen-21-al as the crude product.

b. 2.0 g. of 11β-hydroxy-17α-butyryloxy-3,20-dioxo-4-pregnen-21-al is dissolved in 20 ml. of dimethylformamide and combined with 7 ml. of 2-chloroethanol, 2 ml. of concentrated acetic acid, 4.0 g. of active manganese(IV) oxide, and 320 mg. of potassium cyanide. Teh reaction mixture is agitated for 15 minutes at room temperature. Then, the mixture is filtered off from the manganese(IV) oxide; the filtrate is poured into water and extracted with chloroform. The organic phase is washed with water, dried with sodium sulfate, and concentrated under vacuum. The residue is chromatographed with an acetone-hexane gradient (0–50% acetone) and recyrstallized from acetone/hexane, thus obtaining 905 mg. of the 2-chloroethyl ester of 11β-hydroxy-17α-butyryloxy-3,20-dioxo-4-pregnen-21-oic acid.

EXAMPLE 14

500 mg. of 11β-hydroxy-17α-butyryloxy-3,20-dioxo-4-pregnen-21-al is reacted under the conditions indicated in Example 13(b), but with 2,2,2-trifluoroethanol, thus obtaining the 2,2,2-trifluoroethyl ester of 11β-hydroxy-17α-butyryloxy-3,20-dioxo-4-pregnen-21-oic acid.

EXAMPLE 15

1.0 g. of 11β-hydroxy-17α-benzoyloxy-3,20-dioxo-1,4-pregnadien-21-al, prepared analogously to Example 13(a) is converted, under the conditions described in Example 13(b), into the 2-chloroethyl ester of 11β-hydroxy-17α-benzoyloxy-3,20-dioxo-1,4-pregnadien-21-oic acid.

EXAMPLE 16

250 mg. of 11β-hydroxy-17α-benzoyloxy-3,20-dioxo-1,4-pregnadien-21-al is converted, under the conditions described in Example 13(b) but with 2,2,2-trifluoroethanol, into the 2,2,2-trifluoroethyl ester of 11β-hydroxy-17α-benzoyloxy-3,20-dioxo-1,4-pregnadien-21-oic acid.

EXAMPLE 17

250 mg. of 11β-hydroxy-17α-benzoyloxy-3,20-dioxo-1,4-pregnadien-21-al is converted, under the conditions set forth in Example 13(b) but with 4-fluorobenzyl alcohol, into the 4-fluorobenzyl ester of 11β-hydroxy-17α-benzoyloxy-3,20-dioxo-1,4-pregnadien-21-oic acid.

EXAMPLE 18

2.0 g. of 9α-fluoro-11β-dihydroxy-17α-propionyloxy-3,20-dioxo-4-pregnen-21-al produced according to Example 13(a) is converted, under the conditions set forth in Example 13(b), into the 2-chloroethyl ester of 9α-fluoro-11β-hydroxy-17α-propionyloxy-3,20-dioxo-4-pregnen-21oic acid.

EXAMPLE 19

1.0 g. of 9α-fluoro-11β-hydroxy-17α-propionyloxy-3,20-dioxo-4-pregnen-21-al is converted, under the conditions described in Example 13(b) but with 2,2,2-trichloroethanol, into the 2,2,2-trichloroethyl ester of 9α-fluoro-11β-hydroxy-17-propionyloxy-3,20-dioxo-4-pregnen-21-oic acid.

EXAMPLE 20

500 mg. of 9α-fluoro-11β-hydroxy-17α-acetoxy-3,20-dioxo-16α-methyl-1,4-pregnadien-21-al prepared in accordance with Example 13(a) is converted, under the conditions indicated in Example 13(b), into the 2-chloroethyl ester of 9α-fluoro-11β-hydroxy-17α-acetoxy-3,20-dioxo-16α-*methyl*-1,4-pregnadien 21oic acid.

EXAMPLE 21

500 mg. of 9α-fluoro-11β-hydroxy-17α-acetoxy-3,20-dioxo-16α-methyl-1,4-pregnadien-21-al is converted, under the conditions set forth in Example 13(b) but with 4-fluorobenzyl alcohol, into the 4-fluorobenzyl ester of 9α-fluoro-11β-hydroxy-17α-acetoxy-3,20-dioxo-16α-methyl-1,4-pregnadien-21-oic acid.

EXAMPLE 22

250 mg. of 9α-fluoro-11β-hydroxy-17α-valeryloxy-3,20-dioxo-16β-methyl-1,4-pregnadien-21-al prepared analogously to Example 13(a) is converted, under the conditions described in Example 13(b), into the 2-chloroethyl ester of 9α-fluoro-11β-hydroxy-17α-valeryloxy-3,20-dioxo-16β-methyl-1,4-pregnadien-21-oic acid.

EXAMPLE 23

300 mg. of 11β-hydroxy-17α-acetoxy-3,20-dioxo-6α-methyl-1,4-preganadien-21-al prepared analogously to Example 13(a) is converted, under the conditions described in Example 13(b), into the 2-chloroethyl ester of 11β-hydroxy-17α-acetoxy-3,20-dioxo-6α-methyl-1,4-pregnadien-21-oic acid.

EXAMPLE 24 a. 5.0 g. of 11β-hydroxy-17α-butyryloxy-3,20-dioxo-4-pregnen-21-al is dissolved under a nitrogen atmosphere in 25 ml. of methanol and 150 ml of acetonitrile. This solution is combined with 8 ml. of concentrated acetic acid, 10 g. of manganese(IV) oxide, as well as 1.75 g. of potassium cyanide. The reaction mixture is allowed to react for 8 minutes at room temperature. The manganese dioxide is filtered off, the filtrate is diluted with chloroform, washed with water, and dried over sodium sulfate. After evaporation of the solvent, 6.25 g. of an oil is obtained which is chromatographed on silica gel. With 40–45% of ethyl acetate/hexane and after recrystallization from ether/petroleum ether, the product is 1.8 g. of the methyl ester of 11β-hydroxy-17α-butyryloxy-3,20-dioxo-4-pregnen-21-oic acid.

b. 1.0 g. of the methyl ester of 11β-hydroxy-17α-butyryloxy-3,20-dioxo-4-pregnen-21-oic acid is dissolved in 100 ml. of methanol containing 10% of water. At 0° C., the solution is combined with 1 ml. of 2N sodium hydroxide solution, diluted with water after 15 minutes, and extracted with ether. The aqueous phase is acidified with hydrochloric acid and extracted with ether. After drying over sodium sulfate, the solvent is evaporated under vacuum and the residue is chromatographed on silica gel, thus isolating 315 mg. of 11β-hydroxy-17α-butyryloxy-3,20-dioxo-4-pregnen-21-oic acid.

c. 300 mg. of 11βhydroxy-17α-butyryloxy-3,20-dioxo-4-pregnen-21-oic acid is dissolved in 40 ml. of methanol and combined with 6.7 ml. of a 0.1N solution of sodium hydroxide in methanol. The solution is concentrated under vacuum, and the residue is combined with ether. The thus-precipitated sodium salt of 11β-hydroxy-17α-butyryloxy-3,20-dioxo-4-pregnen-21-oic acid is vacuum-filtered and dried under vacuum. Yield: 325 mg.

d. A solution of 325 mg. of the thus-prepared sodium salt in 5.0 ml. of hexamethylphosphoric triamide is combined with 0.5 ml. of chloroiodomethane and stirred for 30 minutes at room temperature. Subsequently, the reaction mixture is combined with methylene chloride, washed with water, and dried over sodium sulfate. After evaporation of the solvent, the residue is purified by chromatography, thus obtaining 93 mg. of the chloromethyl ester of 11β-hydroxy-17α-butyryloxy-3,20-dioxo-4-pregnen-21-oic acid.

EXAMPLE 25

A solution of 50 mg. of the chloromethyl ester of 11β-hydroxy-17α-butyryloxy-3,20-dioxo-4-pregnen-21-oic acid in 5 ml. of acetonitrile is combined with 259 mg. of silver fluoride and stirred for 5 days at room temperature under the exclusion of light. After filtration, the mixture is combined with methylene chloride, washed with water, dried, and concentrated under vacuum, thus obtaining, after preparative thin-layer chromatography, the fluoromethyl ester of 11β-hydroxy-17α-butyryloxy-3,20-dioxo-4-pregnen-21-oic acid.

EXAMPLE 26

500 mg. of the methyl ester of 11β-hydroxy-17α-butyryloxy-3,20-dioxo-4-pregnen-21-oic acid is dissolved in 15 ml. of 2-chloroethanol. The solution is allowed to stand for 6 days at room temperature. Then, the reaction product is precipitated with water, isolated, and chromatographed on silica gel, thus obtaining 11β-hydroxy-17α-butyryloxy-3,20-dioxo-4-pregnen-21-oic acid 2-chloroethyl ester.

EXAMPLE 27 a. A solution of 1.0 g. of 9α-fluoro-11β,21-dihydroxy-16α,17α-isopropylidenedioxy-1,4-pregnadiene-3,20-dione in 125 ml. of methanol is combined with 250 mg. of copper(II) acetate in 125 ml. of methanol and stirred for 30 minutes while passing air through the mixture. The latter is then diluted with dichloromethane, washed with ammonium chloride and water, dried over sodium sulfate, and evaporated under vacuum. Yield: 1.0 g. of 9α-fluoro-11β-hydroxy-16α,17α-isopropylidenedioxy-3,20-dioxo-1,4-pregnadien-21-al.

b. 150 mg. of the thus-obtained aldehyde is dissolved in 1.5 ml. of dimethylformamide, and the solution is agitated for 30 minutes after the addition of 0.5 ml. of 2-bromoethanol, 24 mg. of potassium cyanide, 0.15 ml. of glacial acetic acid, and 0.3 g. of manganese(IV) oxide. The manganese dioxide is filtered off; the filtrate is diluted with dichloromethane and washed with water, dried, and evaporated under vacuum. Recrystallization from acetone/hexane yields 70 mg. of the 2-bromoethyl ester of 9α-fluoro-11β-hydroxy-16α,17α-isopropylidenedioxy-3,20-dioxo-1,4-pregnadien-21-oic acid, m.p. 261° C. $[\alpha]_D^{25} = +48°$ (chloroform). UV: $\epsilon_{239} = 16,100$ (methanol).

EXAMPLE 28

300 mg. of 9α-fluoro-11β-hydroxy-16α,17α-isopropylidenedioxy-3,20-dioxo-1,4-pregnadien-21-al is reacted under the conditions described in Example 27(b) but with 2-fluoroethanol. After recrystallization from acetone/hexane, 170 mg. of the 2-fluoroethyl ester of 9α-fluoro-11β-hydroxy-16α,17α-isopropylidenedioxy-3,20-dioxo-1,4-pregnadien-21-oic acid is isolated; m.p. 271° C. (decomposition). $[\alpha]_D^{25} = +50°$ (chloroform). UV: $\epsilon_{238} = 15,700$ (methanol).

EXAMPLE 29

500 mg. of 9α-fluoro-11β-hydroxy-16α,17α-isopropylidenedioxy-3,20-dioxo-1,4-pregnadien-21-al is reacted under the conditions described in Example 27(b) but with 2-chloroethanol. The reaction mixture is recrystallized from acetone/hexane, thus isolating 340 mg of the 2-chloroethyl ester of 9α-fluoro-11β-hydroxy-16α,17α-isopropylidenedioxy-3,20-dioxo-1,4-pregnadien-21-oic acid; m.p. 218° C. (decomposition). $[\alpha]_D^{25} = +49°$ (chloroform). UV: $\epsilon_{239} = 15,900$ (methanol).

EXAMPLE 30

1.0 g. of 9α,11β-dichloro-16α,17α-isopropylidenedioxy-3,20-dioxo-1,4-pregnadien-21-al prepared in accordance with Example 27(a) is reacted under the conditions set forth in Example 27(b) but with 2-fluoroethanol. After recrystallization from acetone/hexane, 500 mg. of the 2-fluoroethyl ester of 9α,11β-dichloro-16α,17α-isopropylidenedioxy-3,20-dioxo-1,4-pregnadien-21-oic acid is isolated; m.p. 223° C. (decomposition). $[\alpha]_D^{25} = +100°$ (chloroform). UV: $\epsilon_{237} = 15,300$ (methanol).

EXAMPLE 31

1.0 g. of 9α,11β-dichloro-16α,17α-isopropylidenedioxy-3,20-dioxo-1,4-pregnadien-21-al is reacted under the conditions described in Example 27(b), but with 2-chloroethanol. The reaction mixture is recrystallized from isopropyl ether, thus isolating 320 mg. of the 2-chloroethyl ester of 9α,11β-dichloro-16α,17α-isopropylidenedioxy-3,20-dioxo-1,4-pregnadien-21-oic acid; m.p. 227° C. (decomposition). $[\alpha]_D^{25} = +97°$ (chloroform). UV: $\epsilon_{237} = 15,400$ (methanol).

EXAMPLE 32

950 mg. of 9α-chloro-11β-hydroxy-16α,17α-isopropylidenedioxy-3,20-dioxo-1,4-pregnadien-21-al prepared analogously to Example 27(a) is reacted, under the conditions described in Example 27(b) but with 2-chloroethanol. Recrystallization from acetone/hexane yields 290 mg. of the 2-chloroethyl ester of 9α-chloro-11β-hydroxy-16α,17α-isopropylidenedioxy-3,20-dioxo-1,4-pregnadien-21-oic acid.

EXAMPLE 33

800 mg. of 9α-chloro-16α,17α-isopropylidenedioxy-3,11,20-trioxo-1,4-pregnadien-21-al produced analogously to Example 27(a) is reacted, under the conditions set forth in Example 27(b) but with 2-chloroethanol. Recrystallization from acetone/hexane yields 260 mg. of the 2-chloroethyl ester of 9α-chloro-16α,17α-isopropylidenedioxy-3,11,20-trioxo-1,4-pregnadien-21-oic acid.

EXAMPLE 34 a. 5 g. of 9α-fluoro-11β-hydroxy-16α,17α-isopropylidenedioxy-3,20-dioxo-1,4-pregnadien-21-oic acid is dissolved in 750 ml. of methanol and combined with 111.5 ml. of a 0.1N solution of sodium hydroxide in methanol. The solvent is extensively evaporated under vacuum and the residue combined with 100 ml. of ether. The thus-precipitated sodium salt of 9α-fluoro-11β-hydroxy-16α,17α-isopropylidenedioxy-3,20-dioxo-1,4-pregnadien-21-oic acid is vacuum-filtered and dried under vacuum. Yield: 4.65 g.; m.p. 290° C. $[\alpha]_D^{25} = +34°$ (methanol). UV: $\epsilon_{237} = 15,600$ (methanol).

b. A solution of 4.1 g. of the sodium salt of 9α-fluoro-11β-hydroxy-16α,17α-isopropylidenedioxy-3,20-dioxo-1,4-pregnadien-21-oic acid in 30 ml. of hexamethylphosphoric triamide is combined with 2.9 ml. of chloroiodomethane and agitated for 30 minutes at room temperature. After dilution with ethyl acetate, the mixture is washed neutral with water and dried over sodium sulfate, whereupon the mixture is concentrated under vacuum. The residue is chromatographed on silica gel with a methylene chloride-acetone gradient (0–30% acetone). Yield: 2.2 g. of the chloromethyl ester of 9α-fluoro-11β-hydroxy-16α,17α-isopropylidenedioxy-3,20-dioxo-1,4-pregnadien-21-oic acid; m.p. 261°–263° C. (decomposition). $[\alpha]_D^{25} = +68°$ (pyridine). UV: $\epsilon_{238} = 16,100$ (methanol).

EXAMPLE 35

A solution of 400 mg. of the chloromethyl ester of 9α-fluoro-11β-hydroxy-16α,17α-isopropylidenedioxy-3,20-dioxo-1,4-pregnadien-21-oic acid in 30 ml. of acetonitrile is combined with 750 mg. of silver fluoride and agitated for 5 days under the exclusion of light at room temperature. Thereafter, the mixture is vacuum-filtered over a layer of sodium sulfate, the filtrate is diluted with ethyl acetate, washed with water, dried, and concentrated. After preparative thin-layer chromatography in the system chloroform/acetone = 8:2, the yield is 90 mg. of the fluoromethyl ester of 9α-fluoro-11β-hydroxy-16α,17α-isopropylidenedioxy-3,20-dioxo-1,4-pregnadien-21-oic acid.

EXAMPLE 36

A solution of 2.1 g. of the sodium salt of 9α-chloro-11β-hydroxy-16α,17α-isopropylidenedioxy-3,20-dioxo-1,4-pregnadien-21-oic acid obtained analogously to Example 34(a) is reacted, in accordance with Example 34(b), to the chloromethyl ester of 9α-chloro-11β-hydroxy-16α,17α-isopropylidenedioxy-3,20-dioxo-1,4-pregnadien-21-oic acid. Yield: 1.2 g.

EXAMPLE 37

Analogously to Example 35, 600 mg. of the chloromethyl ester of 9α-chloro-11β-hydroxy-16α,17α-isopropylidenedioxy-3,20-dioxo-1,4-pregnadien-21-oic acid is reacted to obtain 160 mg. of the fluoromethyl ester of 9α-chloro-11β-hydroxy-16α,17α-isopropylidenedioxy-3,20-dioxo-1,4-pregnadien-21-oic acid.

EXAMPLE 38

A solution of 2.5 g. of the sodium salt of 9α-chloro-16α,17α-isopropylidenedioxy-3,11,20-trioxo-1,4-pregnadien-21-oic acid obtained according to Example 34(a) is reacted, in accordance with Example 34(b), to the chloromethyl ester of 9α-chloro-16α,17α-isopropylidenedioxy-3,11,20-trioxo-1,4-pregnadien-21-oic acid. Yield: 1.4 g. Melting point: 224° C. (decomposition). $[\alpha]_D^{25} = +170°$ (pyridine). UV: $\epsilon_{237} = 15,100$ (methanol).

EXAMPLE 39

1.0 g. of the chloromethyl ester of 9α-chloro-16α,17α-isopropylidenedioxy-3,11,20-trioxo-1,4-pregnadien-21-oic acid is reacted, analogously to Example 35, to 240 mg. of the fluoromethyl ester of 9α-chloro-16α,17α-isopropylidenedioxy-3,11,20-trioxo-1,4-pregnadien-21-oic acid.

EXAMPLE 40

A solution of 2.3 g. of the sodium salt of 9α,11β-dichloro-16α,17α-isopropylidenedioxy-3,20-dioxo-1,4-pregnadien-21-oic acid produced according to Example 34(a) is reacted, analogously to Example 34(b), to the chloromethyl ester of 9α,11β-dichloro-16α,17α-isopropylidenedioxy-3,20-dioxo-1,4-pregnadien-21-oic acid. Yield: 1.3 g., m.p. 240°–241° C. (decomposition). $[\alpha]_D^{25} = +108°$ (pyridine). UV: $\epsilon_{237} = 15,300$ (methanol).

EXAMPLE 41

Corresponding to Example 35, 1.0 g. of the chloromethyl ester of 9α,11β-dichloro-16α,17α-isopropylidenedioxy-3,20-dioxo-1,4-pregnadien-21-oic acid is reacted to obtain 220 mg. of the fluoromethyl ester of 9α,11β-dichloro-16α,17α-isopropylidenedioxy-3,20-dioxo-1,4-pregnadien-21-oic acid.

EXAMPLE 42

1.0 g. of 9α-fluoro-11β-hydroxy-16α,17α-isopropylidenedioxy-3,20-dioxo-1,4-pregnadien-21-al is reacted under the conditions described in Example 27(b), but with 2,2,2-trifluoroethanol. Yield: 310 mg. of the 2,2,2-trifluoroethyl ester of 9α-fluoro-11β-hydroxy-16α,17α-isopropylidenedioxy-3,20-dioxo-1,4-pregnadien-21-oic acid.

EXAMPLE 43

1.0 g. of 9α-fluoro-11β-hydroxy-16α,17α-isopropylidenedioxy-3,20-dioxo-1,4-pregnadien-21-al is reacted analogously to Example 27(b), but with 4-fluorobenzyl alcohol, yielding 290 mg. of the 4-fluorobenzyl ester of 9α-fluoro-11β-hydroxy-16α,17α-isopropylidenedioxy-3,20-dioxo-1,4-pregnadien-21-oic acid; m.p. 260°–262° C. $[\alpha]_D^{25} = +42°$ (pyridine). UV: $\epsilon_{237} = 15,200$ (methanol).

EXAMPLE 44

A solution of 645 mg. of the sodium salt of 16α,17α-isopropylidenedioxy-3,20-dioxo-1,4-pregnadien-21-oic acid, obtained in accordance with Example 34(a) yields, analogously to Example 34(b), 275 mg. of the chloromethyl ester of 16α,17α-isopropylidenedioxy-3,20-dioxo-1,4-pregnadien-21-oic acid; m.p. 221° C. $[\alpha]_D = +42°$ (chloroform). UV: $\epsilon_{244} = 16,200$ (methanol).

EXAMPLE 45

A solution of 500 mg. of the butyl ester of 11β-hydroxy-16α,17α-isopropylidenedioxy-3,20-dioxo-1,4-pregnadien-21-oic acid in 10 ml. of 2-chloroethanol is allowed to stand for 8 days at room temperature. The reaction product is isolated by water precipitation and chromatographed on silica gel for purification purposes. Yield: 179 mg. of the 2-chloroethyl ester of 11β-hydroxy-16α,17α-isopropylidenedioxy-3,20-dioxo-1,4-pregnadien-21-oic acid.

EXAMPLE 46

1.4 g. of 6α-fluoro-11β-hydroxy-3,20-dioxo-16α-methyl-1,4-pregnadien-21-al is dissolved in 14 ml. of dimethylformamide and combined with 5 ml. of 2-fluoroethanol, 1.4 ml. of concentrated acetic acid, 2.8 g. of active manganese (IV) oxide, and 225 mg. of potassium cyanide. The reaction mixture is agitated for 10 minutes at room temperature and then filtered off from the manganese (IV) oxide. The filtrate is poured into water and extracted with dichloromethane. The organic phase is washed with water, dried with sodium sulfate, and concentrated under vacuum. The residue is chromatographed on silica gel. With 31–33% acetone-hexane, after recrystallization from acetone/hexane, 630 mg. of the 2-fluoroethyl ester of 6α-fluoro-11β-hydroxy-3,20-dioxo-16α-methyl-1,4-pregnadien-21-oic acid is obtained; m.p. 188.0° C. $[\alpha]_D^{25} = +141°$ (chloroform). UV: $\epsilon_{242} = 16,900$ (methanol)

EXAMPLE 47

5.0 g. of 6α-fluoro-11β-hydroxy-3,20-dioxo-16α-methyl-1,4-pregnadien-21-al is reacted, under the conditions set forth in Example 46, but with 2-chloroethanol in place of 2-fluoroethanol, and then worked up. The crude product is chromatographed on silica gel. With 25–29% acetone-hexane, 2.19 g. of the 2-chloroethyl ester of 6α-fluoro-11β-hydroxy-3,20-dioxo-16α-methyl-1,4-pregnadien-21-oic acid is obtained, m.p. 174.8° C. $[\alpha]_D^{25} = +135°$. UV: $\epsilon_{242} = 17,100$ (methanol).

EXAMPLE 47 A 3.0 g. of the butyl ester of 6α-fluoro-11β-hydroxy-3,20-dioxo-16α-methyl-1,4-pregnadien-21-oic acid is dissolved in 60 ml. of 2-bromoethanol. The solution is maintained for 7 days at room temperature; then, the reaction product is isolated by water precipitation and chromatographed on silica gel for purification. With 27–30% acetone-hexane, after recrystallization from acetone/hexane, 698 mg. of the 2-bromoethyl ester of 6α-fluoro-11β-hydroxy-3,20-dioxo-16α-methyl-1,4-pregnadien-21-oic acid is produced; m.p. 169.5° C. $[\alpha]_D^{25} = +129°$ (chloroform). UV: $\epsilon_{242} = 16,900$ (methanol)

EXAMPLE 48

405 mg. of the 2-bromoethyl ester of 6α-fluoro-11β-hydroxy-3,20-dioxo-16α-methyl-1,4-pregnadien-21-oic acid is dissolved in 13 ml. of acetone and then combined with 1.0 g. of sodium iodide. The reaction mixture is stirred for 12 days at room temperature and then concentrated to dryness. The residue is dissolved in dichloromethane, the solution is washed with water, dried over sodium sulfate, and the solvent is evaporated under vacuum. The residue is chromatographed on silica gel. With 28–34% acetone-hexane and after recrystallization from acetone/hexane, 277 mg. of the 2-iodoethyl ester of 6α-fluoro-11β-hydroxy-3,20-dioxo-16α-methyl-1,4-pregnadien-21-oic acid is obtained; m.p. 208.6° C. $[\alpha]_D^{25} = +122°$ (chloroform). UV: $\epsilon_{242} = 17,000$ (methanol).

EXAMPLE 49

5.0 g. of the sodium salt of 6α-fluoro-11β-hydroxy-3,20-dioxo-16α-methyl-1,4-pregnadien-21-oic acid is dissolved in 25 ml. of hexamethylphosphoric triamide. After the addition of 3 ml. of chloroiodomethane, the mixture is stirred for 20 minutes and then combined with water. The reaction mixture is extracted with ethyl acetate, the organic phase is dried with sodium sulfate and evaporated under vacuum. The residue is chromatographed on silica gel. With 25–29% acetone-hexane, after recrystallization from acetone/hexane, 880 mg. of the chloromethyl ester of 6α-fluoro-11β-hydroxy-3,20-dioxo-16α-methyl-1,4-pregnadien-21-oic acid is obtained; m.p. 183.2° C. $[\alpha]_D^{25} = +155°$ (chloroform). UV: $\epsilon_{242} = 17,200$ (methanol).

EXAMPLE 50

500 mg. of the chloromethyl ester of 6α-fluoro-11β-hydroxy-3,20-dioxo-16α-methyl-1,4-pregnadien-21-oic acid is dissolved in 40 ml. of acetonitrile and combined with 1.0 g. of silver fluoride. The mixture is agitated for 6 days at room temperature under the exclusion of light, filtered through a filter plate, and the filtrate is diluted with dichloromethane. The solution is washed with water, dried over sodium sulfate, and evaporated under vacuum. The residue is chromatographed on silica gel, thus obtaining 110 mg. of the fluoromethyl ester of 6α-fluoro-11β-hydroxy-3,20-dioxo-16α-methyl-1,4-pregnadien-21-oic acid.

EXAMPLE 51 a. A solution of 3.0 g. of the butyl ester of 6α-fluoro-11β-hydroxy-3,20-dioxo-16α-methyl-1,4-pregnadien-21-oic acid in a mixture of 9 ml. of ethylene glycol and 21 ml. of dimethylformamide is combined with 300 mg. of potassium tert.-butylate and agitated for 5 minutes at room temperature. The reaction product is precipitated with water, filtered off, dried, and chromatographed on silica gel. With 30–40% acetone-methylene chloride, after recrystallization from acetone/hexane, 361 mg. of the 2-hydroxyethyl ester of 6α-fluoro-11β-hydroxy-3,20-dioxo-16α-methyl-1,4-pregnadien-21-oic acid is obtained; m.p. 180.8° C. $[\alpha]_D^{25} = +148°$ (chloroform). UV: $\epsilon_{242} = 16,900$ (methanol).

b. 200 mg. of the 2-hydroxyethyl ester of 6α-fluoro-11β-hydroxy-3,20-dioxo-16α-methyl-1,4-pregnadien-21-oic acid is dissolved in 4 ml. of pyridine; the solution is combined with 0.2 ml. of methanesulfonic acid chloride and agitated for 24 hours at room temperature. Subsequently, the mixture is poured into ice water, the thus-precipitated compound is isolated and chromatographed on silica gel with acetone-hexane, thus obtaining, after recrystallization, from acetone/hexane, 87 mg. of the 2-chloroethyl ester of 6α-fluoro-11β-hydroxy-3,20-dioxo-16α-methyl-1,4-pregnadien-21-oic acid.

EXAMPLE 52 a. 3.0 g. of 6α,9α-difluoro-11β-hydroxy-16α-methyl-1,4-pregnadiene-3,20-dione is dissolved in 300 ml. of methanol. After adding 1.0 g. of copper (II) acetate, air is sucked through the solution for 30 minutes and the solution is then combined with saturated ammonium chloride solution. The mixture is extracted with dichloromethane, the organic phase is washed with water and dried over sodium sulfate. After evaporating the solvent under vacuum, 3.3 g. of 6α,9α-difluoro-11β-hydroxy-3,20-dioxo-16α-methyl-1,4-pregnadien-21-al is obtained in the form of a foam.

b. 3.3 g. of 6α,9α-difluoro-11βhydroxy-3,20-dioxo-16α-methyl-1,4-pregnadien-21-al is reacted under the conditions described in Example 46, but with 2-chloroethanol. The crude product is chromatographed on silica gel. With 25–27% acetone-hexane, after recrystallization from acetone/hexane, 1.11 g. of the 2-chloroethyl ester of 6α,9α-difluoro-11β-hydroxy-3,20-dioxo-16α-methyl-1,4-pregnadien-21-oic acid is obtained; m.p. 172.0° C. $[\alpha]_D^{25} = +123°$ (chloroform). UV: $\epsilon_{238} = 17,200$ (methanol).

EXAMPLE 53

4.5 g. of 6α-fluoro-9α-chloro-11β-hydroxy-3,20-dioxo-16α-methyl-1,4-pregnadien-21-al prepared analogously to Example 52(a) is reacted, under the conditions described in Example 46, but with the use of 2-chloroethanol, to the 2-chloroethyl ester of 6α-fluoro-9α-chloro-11β-hydroxy-3,20-dioxo-16α-methyl-1,4-pregnadien-21-oic acid; m.p. 211.1° C. $[\alpha]_D^{25} = +148°$ (chloroform). UV: $\epsilon_{238} = 17,100$ (methanol).

EXAMPLE 54

1.0 g. of 6α-fluoro-11β-hydroxy-3,20-dioxo-16α-methyl-1,4-pregnadien-21-al is reacted, under the conditions described in Example 46 but with 2,2,2-trifluoroethanol, thus obtained the 2,2,2-trifluoroethyl ester of 6α-fluoro-11β-hydroxy-3,20-dioxo-16α-methyl-1,4-pregnadien-21-oic acid, m.p. 192.9° C. $[\alpha]_D^{25} = +130°$ (chloroform). UV: $\epsilon_{242} = 17,000$ (methanol).

EXAMPLE 55

2.0 g. of 6α-fluoro-11β-hydroxy-3,20-dioxo-16α-methyl-1,4-pregnadien-21-al is converted, under the conditions described in Example 46 but with 2,2,2-trichloroethanol, into the 2,2,2-trichloroethyl ester of 6α-fluoro-11β-hydroxy-3,20-dioxo-16α-methyl-1,4-pregnadien-21-oic acid; m.p. 196.5° C. $[\alpha]_D^{25} = +121°$ (chloroform). UV: $\epsilon_{242} = 17,100$ (methanol).

EXAMPLE 56

2.0 g. of 6α-fluoro-11β-hydroxy-3,20-dioxo-16α-methyl-1,4-pregnadien-21-al is converted, under the conditions described in Example 46 but with 4-fluorobenzyl alcohol, into the 4-fluorobenzyl ester of 6α-fluoro-11β-hydroxy-3,20-dioxo-16α-methyl-1,4-pregnadien-21-oic acid; m.p. 164.7° C. $[\alpha]_D^{25} = +126°$ (chloroform). UV: $\epsilon_{242} = 17,100$ (methanol).

EXAMPLE 57

1.5 g. of 6α-fluoro-2-chloro-11β-hydroxy-3,20-dioxo-16α-methyl-1,4-pregnadien-21-al prepared analogously to Example 52(a) is converted, under the conditions indicated in Example 46 but with 2-chloroethanol, into the 2-chloroethyl ester of 6β-fluoro-2-chloro-11β-hydroxy-3,20-dioxo-16α-methyl-1,4-pregnadien-21-oic acid.

EXAMPLE 58

2.0 g. of 6α,11β-difluoro-9α-chloro-3,20-dioxo-16α-methyl-1,4-pregnadien-21-al produced analogously to Example 52(a) is converted, under the conditions set forth in Example 46 but using 2-chloroethanol, into the 2-chloroethyl ester of 6α,11β-difluoro-9α-chloro-3,20-dioxo-16α-methyl-1,4-pregnadien-21-oic acid.

EXAMPLE 59

1.1 g. of 11β-hydroxy-3,20-dioxo-1,4-pregnadien-21-al produced in accordance with Example 52(a) is converted, under the conditions indicated in Example 46 but with 2-chloroethanol, into the 2-chloroethyl ester of 11β-hydroxy-3,20-dioxo-1,4-pregnadien-21-oic acid.

EXAMPLE 60

1.2 g. of 11β-hydroxy-3,20-dioxo-1,4-pregnadien-21-al is converted, under the conditions set forth in Example 46 but using 2,2,2-trifluoroethanol, into the 2,2,2-trifluoroethyl ester of 11β-hydroxy-3,20-dioxo-1,4-pregnadien-21-oic acid.

EXAMPLE 61

500 mg. of 11β-hydroxy-3,20-dioxo-16α-methyl-1,4-pregnadien-21-al prepared analogously to Example 52(a) is converted, under the conditions indicated in Example 46 but with 4-fluorobenzyl alcohol, into the 4-fluorobenzyl ester of 11β-hydroxy-3,20-dioxo-16α-methyl-1,4-pregnadien-21-oic acid.

EXAMPLE 62

700 mg. of 11β-hydroxy-3,20-dioxo-16α-methyl-4-pregnen-21-al, prepared analogously to Example 52(a) is converted, under the conditions set forth in Example 46, into the 2-fluoroethyl ester of 11β-hydroxy-3,20-dioxo-16α-methyl-4-pregnen-21-oic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and within departing from the spirit and scope thereof, can make various changes and modifications of the invention to adapt it to various usages and conditions.

What is claimed is:

1. A pregnanoic acid compound of the formula

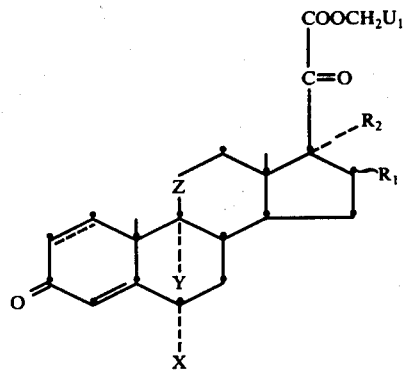

wherein ---- is a single bond or a double bond; X is hydrogen, fluorine or methyl; Y is hydrogen, fluorine or chlorine; Z is β-hydroxymethylene, β-alkanoyloxymethylene of 1-8 carbon atoms in the alkanoyl, β-fluoromethylene, β-chloromethylene, carbonyl or methylene; $R_1$ is hydrogen, methyl in the α- or β-position or methylene and $R_2$ is hydrogen, hydroxy, alkanoyloxy of 1-8 carbon atoms or benzoyloxy or $R_1$ and $R_2$ collectively are alkylidenedioxy of up to 6 carbon atoms; and $U_1$ is halogen, halogenated alkyl of 1-5 carbon atoms or halogenated phenyl with the provision that when $R_2$ is hydrogen, $U_1$ is halogenated phenyl.

2. A pregnanoic acid compound of claim 1 wherein $U_1$ is fluorine or chlorine.

3. A pregnanoic acid compound of claim 1 wherein $U_1$ is fluoromethyl, chloromethyl, trifluoromethyl or trichloromethyl.

4. A pregnanoic acid compound of claim 1 wherein $U_1$ is p-fluorophenyl.

5. A pregnanoic acid compound of claim 1 wherein Z is β-hydroxymethylene.

6. A pregnanoic acid compound of Claim 1 wherein $R_1$ is hydrogen, methyl in the α1 or β-position or methylene and $R_2$ is hydrogen, hydroxy or alkanoyloxy of 1-8 carbon atoms.

7. A pregnanoic acid compound of claim 1 wherein $R_1$ and $R_2$ collectively are alkylidendioxy of up to 6 carbon atoms.

8. A pregnanoic acid compound of claim 1 wherein $R_1$ and $R_2$ collectively are isopropylidenedioxy.

9. 2-Chloroethyl ester of 11β,17α-dihydroxy-3,20-dioxo-1,4-pregnadien-21-oic acid, a compound of claim 1.

10. 2-Fluoroethyl ester of 11β,17α-dihydroxy-3,20-dioxo-1,4-pregnadien-21-oic acid, a compound of claim 1.

11. 2-Chloroethyl ester of 9α-fluoro-11β,17α-dihydroxy-16α-methyl-3,20-dioxo-1,4-pregnadien-21-oic acid, a compound of claim 1.

12. Chloromethyl ester of 11β,17α-dihydroxy-3,20-dioxo-1,4-pregnadien-21-oic acid, a compound of claim 1.

13. Fluoromethyl ester of 11β,17α-dihydroxy-3,20-dioxo-1,4-pregnadien-21-oic acid, a compound of claim 1.

14. 2-Chloroethyl ester of 9α-fluoro-11β,17α-dihydroxy-16α-methyl-3,20-dioxo-1,4-pregnadien-21-oic acid, a compound of claim 1.

15. 2-Fluoroethyl ester of 11β,17α-dihydroxy-6α-methyl-1,4-pregnadien-21-oic acid, a compound of claim 1.

16. 2-Chloroethyl ester of 11β,17α-dihydroxy-3,20-dioxo-16-methylene-1,4-pregnadien-21-oic acid, a compound of claim 1.

17. 2,2,2-Trifluoroethyl ester of 11β,17α-dihydroxy-3,20-dioxo-1,4-pregnadien-21-oic acid, a compound of claim 1.

18. 2,2,2-Trichloroethyl ester of 11β,17α-dihydroxy-3,20-dioxo-1,4-pregnadien-21-oic acid, a compound of claim 1.

19. 4-Fluorobenzyl ester of 11β,17α-dihydroxy-3,20-dioxo-1,4-pregnadien-21-oic acid, a compound of claim 1.

20. 2-Chloroethyl ester of 11β-hydroxy-17α-butyryloxy-3,20-dioxo-4-pregnen-21-oic acid, a compound of claim 1.

21. 2,2,2-Trifluoroethyl ester of 11β-hydroxy-17α-butyryloxy-3,20-dioxo-4-pregnen-21-oic acid, a compound of claim 1.

22. 2-Chloroethyl ester of 11β-hydroxy-17α-acetoxy-3,20-dioxo-6α-methyl-1,4-pregnadien-21-oic acid, a compound of claim 1.

23. 2-Chloroethyl ester of 11β-hydroxy-17α-benzoyloxy-3,20-dioxo-1,4-pregnadien-21-oic acid, a compound of claim 1.

24. 2,2,2-Trifluoroethyl ester of 11β-hydroxy-17α-benzoyloxy-3,20-dioxo-1,4-pregnadien-21-oic acid, a compound of claim 1.

25. 4-Fluorobenzyl ester of 11β-hydroxy-17α-benzoyloxy-3,20-dioxo-1,4-pregnadien-21-oic acid, a compound of claim 1.

26. 2-Chloroethyl ester of 9α-fluoro-11β-hydroxy-17α-propionyloxy-3,20-dioxo-4-pregnen-21-oic acid, a compound of claim 1.

27. 2,2,2-Trichloroethyl ester of 9α-fluoro-11β-hydroxy-17α-propionyloxy-3,20-dioxo-4-pregnen-21-oic acid, a compound of claim 1.

28. 2-Chloroethyl ester of 9α-fluoro-11β-hydroxy-17α-acetoxy-3,20-dioxo-16α-methyl-1,4-pregnadien-21-oic acid, a compound of claim 1.

29. 4-Fluorobenzyl ester of 9α-fluoro-11β-hydroxy-17α-acetoxy-3,20-dioxo-16α-methyl-1,4-pregnadien-21-oic acid, a compound of claim 1.

30. 2-Chloroethyl ester of 9α-fluoro-11β-hydroxy-17α-valeryloxy-3,20-dioxo-16β-methyl-1,4-pregnadien-21-oic acid, a compound of claim 1.

31. 2-chloroethyl ester of 11β-hydroxy-17α-acetoxy-3,20-dioxo-6α-methyl-1,4-pregnadien-21-oic acid, a compound of claim 1.

32. Chloromethyl ester of 11β-hydroxy-17α-butyryloxy-3,20-dioxo-4-pregnen-21-oic acid, a compound of claim 1.

33. Fluoromethyl ester of 11β-hydroxy-17α-butyryloxy-3,20-dioxo-4-pregnen-21-oic acid, a compound of claim 1.

34. 2-Bromoethyl ester of 9α-fluoro-11β-hydroxy-16α,17α-isopropylidenedioxy-3,20-dioxo-1,4-pregnadien-21-oic acid, a compound of claim 1.

35. 2-Fluoroethyl ester of 9α-fluoro-11β-hydroxy-16α,17α-isopropylidenedioxy-3,20-dioxo-1,4-pregnadien-21-oic acid, a compound of Claim 1.

36. 2-Chloroethyl ester of 9α-fluoro-11β-hydroxy-16α,17α-isopropylidenedioxy-3,20-dioxo-1,4-pregnadien-21-oic acid, a compound of claim 1.

37. 2-Fluoroethyl ester of 9α,11β-dichloro-16α,17α-isopropylidenedioxy-3,20-dioxo-1,4-pregnadien-21-oic acid, a compound of claim 1.

38. 2-Chloroethyl ester of 9α,11β-dichloro-16α,17α-isopropylidenedioxy-3,20-dioxo-1,4-pregnadien-21-oic acid, a compound of claim 1.

39. 2-Chloroethyl ester of 9α-chloro-11β-hydroxy-16α,17α-isopropylidenedioxy-3,20-dioxo-1,4-pregnadien-21-oic acid, a compound of claim 1.

40. 2-Chloroethyl ester of 9α-chloro-16α,17α-isopropylidenedioxy-3,11,20-trioxo-1,4-pregnadien-21-oic acid, a compound of claim 1.

41. Chloromethyl ester of 9α-fluoro-11β-hydroxy-16α,17α-isopropylidenedioxy-3,20-dioxo-1,4-pregnadien-21-oic acid, a compound of claim 1.

42. Fluoromethyl ester of 9α-fluoro-11β-hydroxy-16α,17α-isopropylidenedioxy-3,20-dioxo-1,4-pregnadien-21-oic acid, a compound of claim 1.

43. Chloromethyl ester of 9α-chloro-11β-hydroxy-16α,17α-isopropylidenedioxy-3,20-dioxo-1,4-pregnadien-21-oic acid, a compound of claim 1.

44. Fluoromethyl ester of 9α-chloro-11β-hydroxy-16α,17α-isopropylidenedioxy-3,20-dioxo-1,4-pregnadien-21-oic acid, a compound of claim 1.

45. Chloromethyl ester of 9α-chloro-16α,17α-isopropylidenedioxy-3,11,20-trioxo-1,4-pregnadien-21-oic acid, a compound of claim 1.

46. Fluoromethyl ester of 9α-chloro-16α,17α-isopropylidenedioxy-3,11,20-trioxo-1,4-pregnadien-21-oic acid, a compound of claim 1.

47. Chloromethyl ester of 9α,11β-dichloro-16α,17α-isopropylidenedioxy-3,20-dioxo-1,4-pregnadien-21-oic acid, a compound of claim 1.

48. Fluoromethyl ester of 9α,11β-dichloro-16α,17α-isopropylidenedioxy-3,20-dioxo-1,4-pregnadien-21-oic acid, a compound of claim 1.

49. 2,2,2-Trifluoroethyl ester of 9α-fluoro-11β-hydroxy-16α,17α-isopropylidenedioxy-3,20-dioxo-1,4-pregnadien-21-oic acid, a compound of claim 1.

50. 4-Fluorobenzyl ester of 9α-fluoro-11β-hydroxy-16α,17α-isopropylidenedioxy-3,20-dioxo-1,4-pregnadien-21-oic acid, a compound of claim 1.

51. Chloromethyl ester of 16α,17α-isopropylidenedioxy-3,20-dioxo-1,4-pregnadien-21-oic acid, a compound of claim 1.

52. A pregnanoic acid compound of the formula

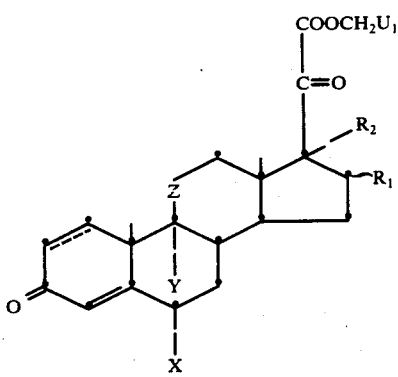

wherein ---- is a single bond or a double bond; X is hydrogen, fluorine or methyl; Y is hydrogen, fluorine or chlorine; Z is β-hydroxymethylene; R₁ is hydrogen, methyl in the α- or β-position or methylene and R₂ is hydrogen; and U₁ is chloromethyl, fluoromethyl, 2-chloroethyl, 2-fluoroethyl, 2-bromoethyl, 2-iodoethyl, 2,2,2-trifluoroethyl, 2,2,2-trichloroethyl, or halogenated phenyl.

53. 2-Chloroethyl ester of 11β-hydroxy-16α,17α-isopropylidenedioxy-3,20-dioxo-1,4-pregnadien-21-oic acid, a compound of claim 1.

54. 2-Fluoroethyl ester of 6α-fluoro-11β-hydroxy-3,20-dioxo-16α-methyl-1,4-pregnadien-21-oic acid, a compound of claim 52.

55. 2-chloroethyl ester of 6α-fluoro-11β-hydroxy-3,20-dioxo-16α-methyl-1,4-pregnadien-21-oic acid, a compound of claim 52.

56. 2-Bromoethyl ester of 6α-fluoro-11β-hydroxy-3,20-dioxo-16α-methyl-1,4-pregnadien-21-oic acid, a compound of claim 52.

57. 2-Iodoethyl ester of 6α-fluoro-11β-hydroxy-3,20-dioxo-16α-methyl-1,4-pregnadien-21-oic acid, a compound of claim 52.

58. Chloromethyl ester of 6α-fluoro-11β-hydroxy-3,20-dioxo-16α-methyl-1,4-pregnadien-21-oic acid, a compound of claim 52.

59. Fluoromethyl ester of 6α-fluoro-11β-hydroxy-3,20-dioxo-16α-methyl-1,4-pregnadien-21-oic acid, a compound of claim 52.

60. 2-Chloroethyl ester of 11β-hydroxy-3,20-dioxo-1,4-pregnadien-21-oic acid, a compound of claim 52.

61. 2-Chloroethyl ester of 6α,9α-difluoro-11β-hydroxy-3,20-dioxo-16α-methyl-1,4-pregnadien-21-oic acid, a compound of claim 52.

62. 2-Chloroethyl ester of 6α-fluoro-9α-chloro-11β-hydroxy-3,20-dioxo-16α-methyl-1,4-pregnadien-21-oic acid, a compound of claim 52.

63. 2,2,2-Trifluoroethyl ester of 6α-fluoro-11β-hydroxy-3,20-dioxo-16α-methyl-1,4-pregnadien-21-oic acid, a compound of claim 52.

64. 2,2,2-Trichloroethyl ester of 6α-fluoro-11β-hydroxy-3,20-dioxo-16α-methyl-1,4-pregnadien-21-oic acid, a compound of claim 52.

65. 4-Fluorobenzyl ester of 6α-fluoro-11β-hydroxy-3,20-dioxo-16α-methyl-1,4-pregnadien-21-oic acid, a compound of claim 52.

66. 2-Chloroethyl ester of 6α-fluoro-2-chloro-11β-hydroxy-3,20-dioxo-16α-methyl-1,4-pregnadien-21-oic acid, a compound of claim 52.

67. 2-Chloroethyl ester of 6α,11β-difluoro-9α-chloro-3,20-dioxo-16α-methyl-1,4-pregnadien-21-oic acid, a compound of claim 52.

68. 2,2,2-Trifluoroethyl ester of 11β-hydroxy-3,20-dioxo-1,4-pregnadien-21-oic acid, a compound of claim 52.

69. 4-Fluorobenzyl ester of 11β-hydroxy-3,20-dioxo-16α-methyl-1,4-pregnadien-21-oic acid, a compound of claim 52.

70. 2-Fluoroethyl ester of 11β-hydroxy-3,20-dioxo-16α-methyl-4-pregnen-21-oic acid, a compound of claim 52.

71. A topically-effective anti-inflammatory pharmaceutical preparation comprising a compound of claim 1, in admixture with a pharmaceutically acceptable carrier.

72. A method of treating mammals afflicted with skin diseases comprising applying to the diseased area an amount of a compound of claim 1, in admixture with a pharmaceutically acceptable carrier, effective to alleviate inflammation caused by the skin disease.

73. The method of claim 72, wherein the compound is applied in the form of a lotion or ointment containing 0.001 to 0.1% by weight of said compound.

74. A method for preparing a pregnanoic acid compound of the formula

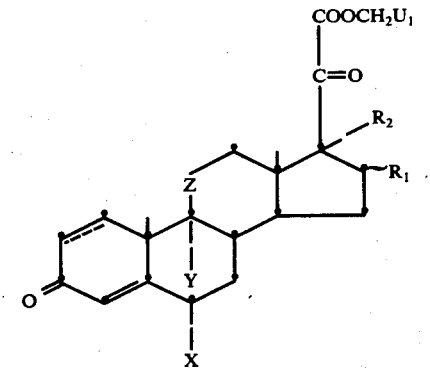

wherein ---- is a single bond or a double bond; X is hydrogen, fluorine or methyl; Y is hydrogen, fluorine or chlorine; Z is β-hydroxymethylene, β-alkanoyloxymethylene of 1-8 carbon atoms in the alkanoyl, β-fluoromethylene, β-chloromethylene, carbonyl or methylene; R₁ is hydrogen, methyl in the α- or β-position or methylene and R₂ is hydrogen, hydroxy, alkanoyloxy of 1-8 carbon atoms or benzoyloxy or R₁ and R₂ collectively are alkylidenedioxy of up to 6 atoms; and wherein U₁ is halogenated alkyl of 1-5 carbon atoms or halogenated phenyl, comprising treating a compound of the formula

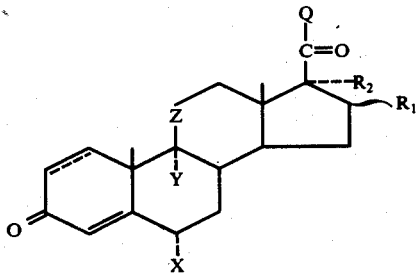

wherein Q is formyl, including hydrates and hemiacetals thereof, with an aliphatic alcohol of the formula

HO—CH₂U₂ wherein $U_2$ is halogenated alkyl of 1-5 carbon atoms or halogenated phenyl, in a mixture of lower aliphatic alcohol and a dipolar aprotic solvent, buffered to pH 4-7 and containing cyanide ions, in the presence of atmospheric oxygen or manganese (IV) oxide.

75. A pregnanoic acid compound of claim 1, wherein $R_2$ is hydroxy, alkanoyloxy of 1-8 carbon atoms or benzoyloxy or $R_1$ and $R_2$ collectively are alkylidenedioxy of up to 6 carbon atoms.

76. A topically-effective anti-inflammatory pharmaceutical preparation comprising a compound of claim 75 in admixture with a pharmaceutically acceptable carrier.

77. A method of treating mammals afflicted with skin diseases comprising applying to the diseased area an amount of a compound of claim 75, in admixture with a pharmaceutically acceptable carrier, effective to alleviate inflammation caused by the skin disease.

78. The method of claim 77, wherein the compound is applied in the form of a lotion or ointment containing 0.001 to 0.1% by weight of said compound.

79. A topically-effective anti-inflammatory pharmaceutical preparation comprising a compound of claim 52, in admixture with a pharmaceutically acceptable carrier.

80. A method of treating mammals afflicted with skin diseases comprising applying to the diseased area an amount of a compound of claim 52, in admixture with a pharmaceutically acceptable carrier, effective to alleviate inflammation caused by the skin disease.

81. The method of claim 80, wherein the compound is applied in the form of a lotion or ointment containing 0.001 to 0.1% by weight of said compound.

* * * * *

UNITED STATES PATENT AND TRADEMARK OFFICE
CERTIFICATE OF CORRECTION

PATENT NO. : 4,049,804
DATED : September 20, 1977
INVENTOR(S) : HENRY LAURENT ET AL.

It is certified that error appears in the above-identified patent and that said Letters Patent are hereby corrected as shown below:

Claim 6, column 20, line 54: Change "al" to -- a --.

Claim 14, column 21, line 11: Change "16α-methyl" to -- 16β-methyl --.

Claim 55, column 23, line 31: Change "2-chloroethyl" to -- 2-Chloroethyl --.

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*